United States Patent [19]
Nowak et al.

[11] Patent Number: 6,121,755
[45] Date of Patent: Sep. 19, 2000

[54] OPTICAL-ELECTRONIC BATTERY INDICATOR

[75] Inventors: David R. Nowak, Bloomingdale; Eric G. Parker, Chicago; Ryan Lindsay, Hampshire, all of Ill.

[73] Assignee: Illinois Tool Works Inc., Glenview, Ill.

[21] Appl. No.: 09/324,519

[22] Filed: Jun. 3, 1999

[51] Int. Cl.[7] ................................................. H02J 7/00
[52] U.S. Cl. .......................................... 320/132; 320/130
[58] Field of Search .................................... 320/132, 130, 320/107; 429/90, 91; 324/426, 432

[56] References Cited

U.S. PATENT DOCUMENTS

| | | | |
|---|---|---|---|
| 3,893,339 | 7/1975 | Melone | 73/327 |
| 4,284,951 | 8/1981 | Dahl et al. | 324/430 |
| 4,320,291 | 3/1982 | Uramoto | 429/91 |
| 4,329,406 | 5/1982 | Dahl et al. | 429/92 |
| 4,388,584 | 6/1983 | Dahl et al. | 320/126 |
| 4,394,613 | 7/1983 | Cole | 320/164 |
| 4,465,963 | 8/1984 | Iseard | 320/147 |
| 4,803,416 | 2/1989 | Abiven et al. | 320/132 |
| 5,218,287 | 6/1993 | Chen | 320/106 |
| 5,245,410 | 9/1993 | Yuste et al. | 356/445 |
| 5,345,163 | 9/1994 | Gibbons et al. | 320/163 |
| 5,481,177 | 1/1996 | Hamley | 320/111 |
| 5,487,956 | 1/1996 | Bromley et al. | 320/163 |
| 5,510,694 | 4/1996 | Nilssen | 320/107 |
| 5,581,170 | 12/1996 | Mammano et al. | 320/116 |
| 5,592,070 | 1/1997 | Mino | 320/163 |
| 5,596,258 | 1/1997 | Kimura et al. | 320/163 |
| 5,629,774 | 5/1997 | Peacock et al. | 356/445 |
| 5,659,238 | 8/1997 | Faulk et al. | 320/136 |
| 5,804,944 | 9/1998 | Alberkrack et al. | 320/163 |

OTHER PUBLICATIONS

Robert Pudlo, Development and Material Selection for a State of Charge Indicator (Mar. 1988) (M.S. thesis, University of Toledo).

*Primary Examiner*—Peter S. Wong
*Assistant Examiner*—Lawrence Luk

[57] ABSTRACT

An optical-electronic device measuring a charge level in a battery having a housing positioned within an interior of the battery, the housing having a cavity. A light source and a light receiving device are positioned within the cavity. A sensing surface and at least one reflecting surface are positioned within the cavity between the light source and the light receiving device. A box is formed with respect to the housing, the at least one reflecting surface dividing the box from the cavity. Light projected from the light source is transmitted from the sensing surface, where a portion of the light is refracted depending upon the charge level of the battery. The remaining light is transmitted to the at least one reflecting surface and then to the light receiving device. A level of charge is thereby determined based upon the amount of light sensed by the light receiving device.

24 Claims, 3 Drawing Sheets

OPTICAL-ELECTRONIC BATTERY INDICATOR

BACKGROUND OF THE INVENTION

1. Field of the Invention

This invention relates to an optical-electronic device for detecting a charge level in a battery.

2. Description of Prior Art

Batteries are commonly used in a variety of applications requiring power including in connection with vehicles for starting, lighting, ignition and various other accessories requiring a power supply. Lead-acid batteries are commonly used in connection with vehicles and typically use lead dioxide as the positive active material and metallic lead as the negative active material, all in an electrolyte of sulfuric acid solution. As the battery progresses from charged to discharged, a specific gravity of the sulfuric acid solution decreases. Likewise, when the battery is in a highly charged state, the specific gravity of the sulfuric acid solution is correspondingly high.

The change in specific gravity of the sulfuric acid, or other electrolyte known to those having ordinary skill in the art, is used in prior art battery charge detectors such as in the device taught by Melone, U.S. Pat. No. 3,893,339. The Melone patent teaches a mechanical device wherein a colored ball floats into the focal point of a light pipe depending upon the specific gravity of the electrolyte. The output end of the light pipe thereby reflects the color of the ball when the battery is in a charged state.

However, in addition to the change in specific gravity of the electrolyte in connection with a change in charge state, the index of refraction of the electrolyte changes as well. As the battery progresses from charged to discharged, the index of refraction of the electrolyte decreases in connection with the decrease in the specific gravity. Likewise, the index of refraction increases as the battery is charged. When light is transmitted into the electrolyte, a drop in the index of refraction of the electrolyte causes a decrease of light refracted into the electrolyte.

SUMMARY OF THE INVENTION

An optic-electronic device for measuring a charge level in a battery preferably comprises a housing positioned with in an interior of the battery. The housing includes a cavity or similar portion for containment of any necessary optics and/or electronics required by this invention.

A light source, such as an LED, is preferably positioned within the cavity of the housing. A light receiving device, such as a photodiode, is also preferably positioned within the cavity of the housing.

A sensing surface is positioned to divide the cavity from the interior of the battery between the light source and the interior of the battery. At least one light reflecting surface is preferably positioned adjacent to the sensing surface. The light receiving device is positioned so that light projected from the light source is transmitted from the sensing surface to the reflecting surface and finally to the light receiving device.

A box is preferably formed with respect to the housing to maximize reflection through the housing. The box is preferably positioned so that at least one reflecting surface divides the box from the cavity and so that the reflecting surface is positioned between the box and the light source.

The sensing surface is preferably spaced apart from the reflecting surface to form an optical void within the housing. The optical void directs light at unwanted angles out of the housing and away from the reflecting surface.

A temperature sensor may additionally be positioned within the cavity of the housing. The temperature sensor preferably senses a temperature within the interior of the battery.

The light receiving device is preferably in communication with a computer, such as through a controller. The controller accepts output from the light receiving device and/or the temperature sensor and transmits appropriate information to the computer for processing and possible feedback. The controller generates a signal based upon the level of charge and/or the internal temperature and if necessary generates a signal to the computer that turns the battery off at a specified state of charge, thereby resulting in optimum battery life and optimum battery operating conditions.

It is one object of this invention to provide a device for measuring a charge in a battery wherein any required optics and electronics are entirely self-contained within a housing.

It is another object of this invention to provide a device for measuring a charge in a battery wherein transmitted light is lost to refraction based upon the specific density of a fluid within the battery.

It is still another object of this invention to provide a device for measuring a charge in a battery comprising similar dimensions as existing devices and for use in connection with a variety of battery sizes and configurations.

It is another object of this invention to provide a device for measuring a charge in a battery that compensates for changes in temperature within the battery.

It is yet another object of this invention to provide a device for measuring a charge in a battery wherein at least one reflecting surface is connected with respect to a box.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
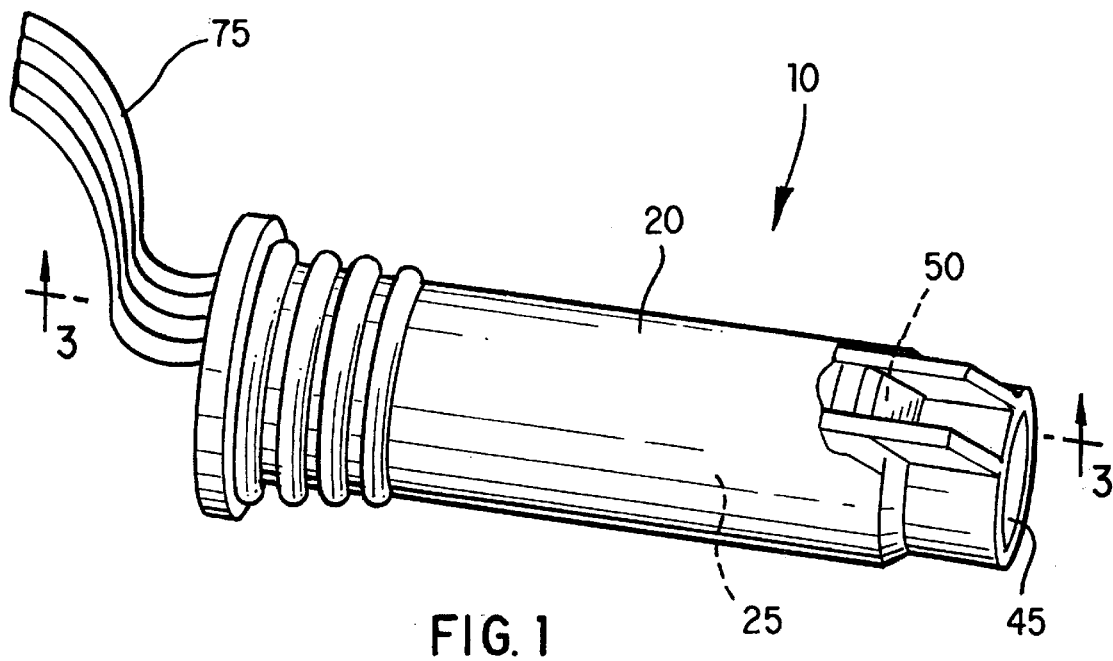
FIG. 1 is a perspective side view of a device according to one preferred embodiment of this invention.
Figure 2:
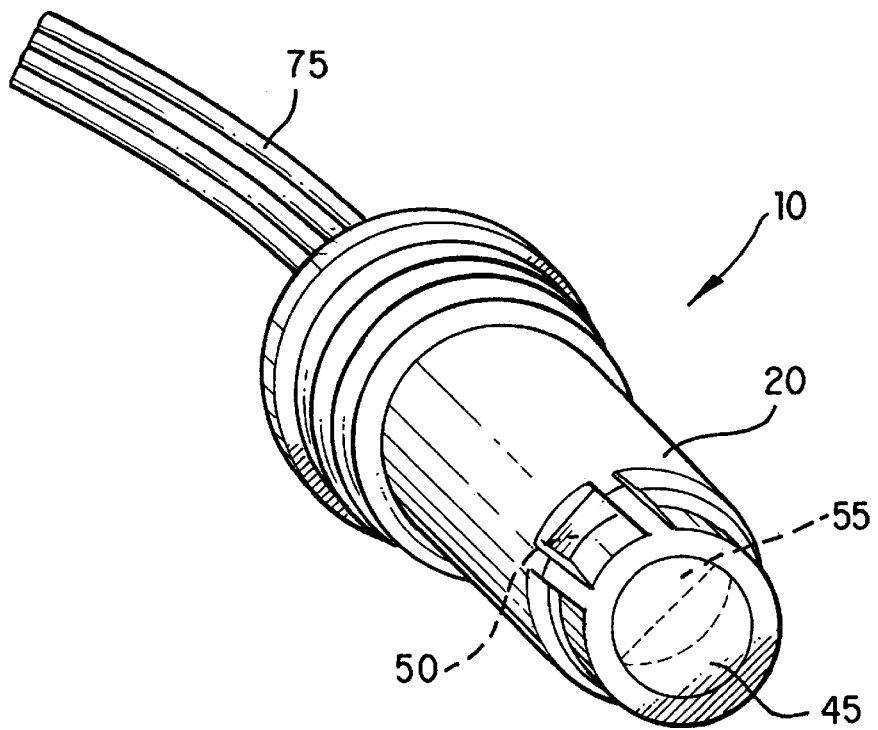
FIG. 2 is a perspective bottom view of the device shown in FIG. 1

FIGS. 1 and 2 show an optical-electronic device 10 for measuring a charge level in a battery. Housing 20 of device 10 is preferably configured in a similar shape and size as existing battery charge sensors.

Device 10 preferably comprises housing 20 positioned within interior 30 of the battery. Batteries typically contain a solution of sulfuric acid which may contaminate and deteriorate many conventional materials. Therefore, housing 20 is preferably molded from styrene acrylonitrile (SAN) or similar material having strong chemical resistant properties. Housing 20 may be constructed from any known chemical resistant, workable, light reflecting material known to those having ordinary skill in the art.

Housing 20 preferably includes cavity 25 or similar interior portion for containment of any necessary optics and/or electronics required by this invention. Cavity 25 may be sealed from the exterior of the housing to prevent contamination 20 of the contained components from water, dirt, battery acid and other potential contaminants. Alternatively, cavity 25 may be unsealed because only approximately 0.001" of air is required within box 45 to optimize reflection on reflecting surface 55.

Figure 3:
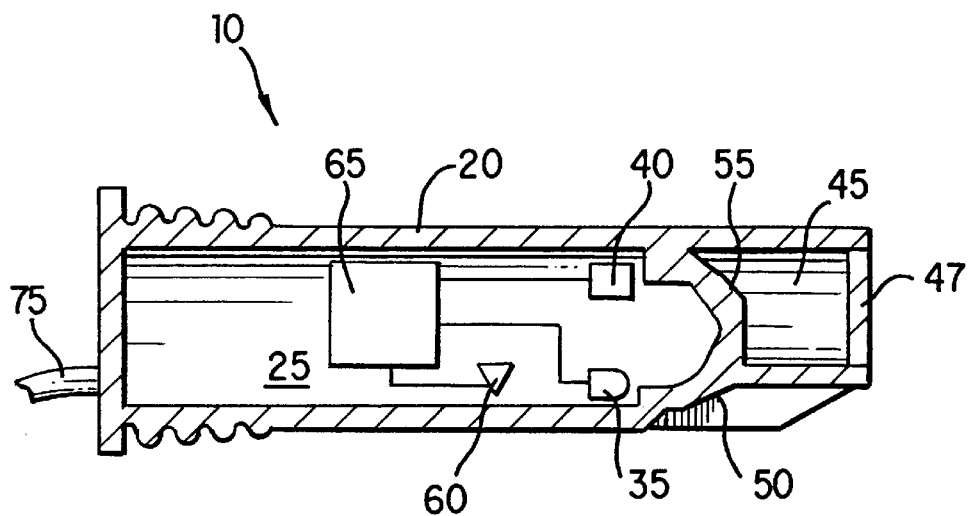
FIG. 3 is a cross-sectional view of the device shown in FIG. 1, including a schematic side view of internal components of the device according to one preferred embodiment of this invention.
Figure 4:
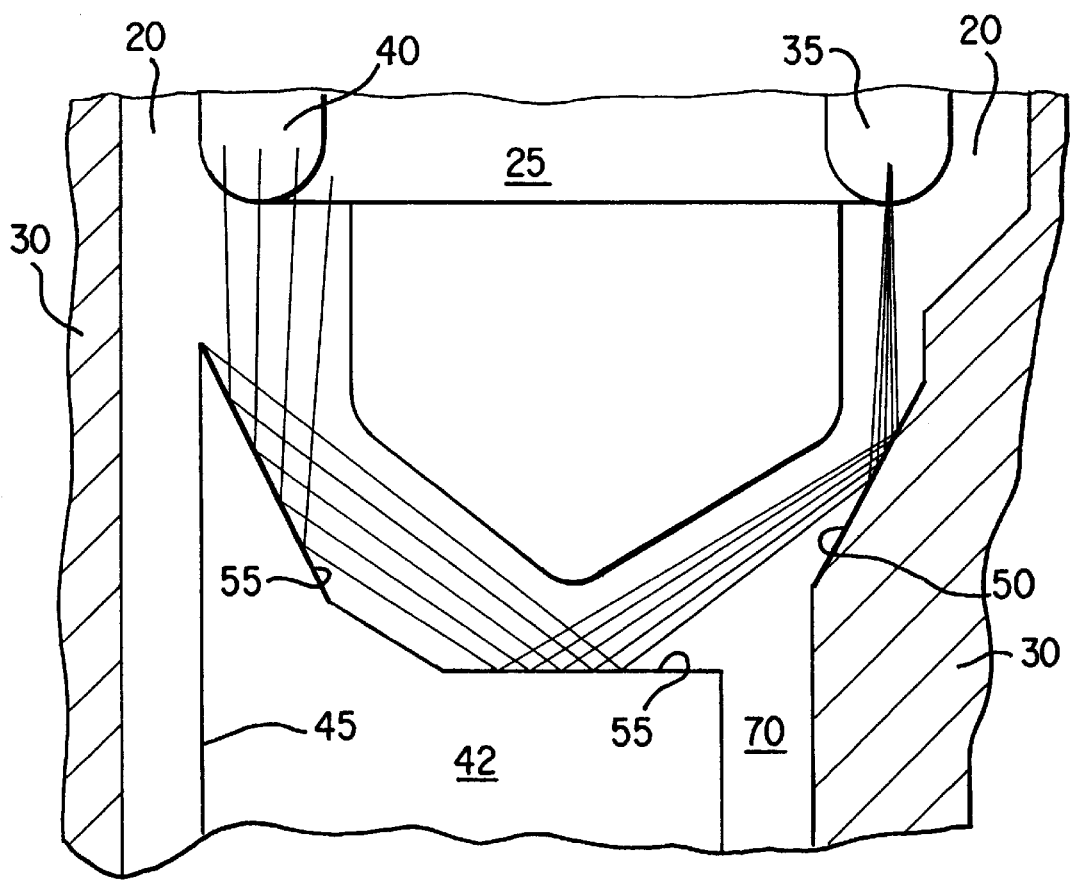
FIG. 4 is a schematic representation of light transmission patterns within a housing when a battery is in a low charge state according to one preferred embodiment of the invention.
Figure 5:
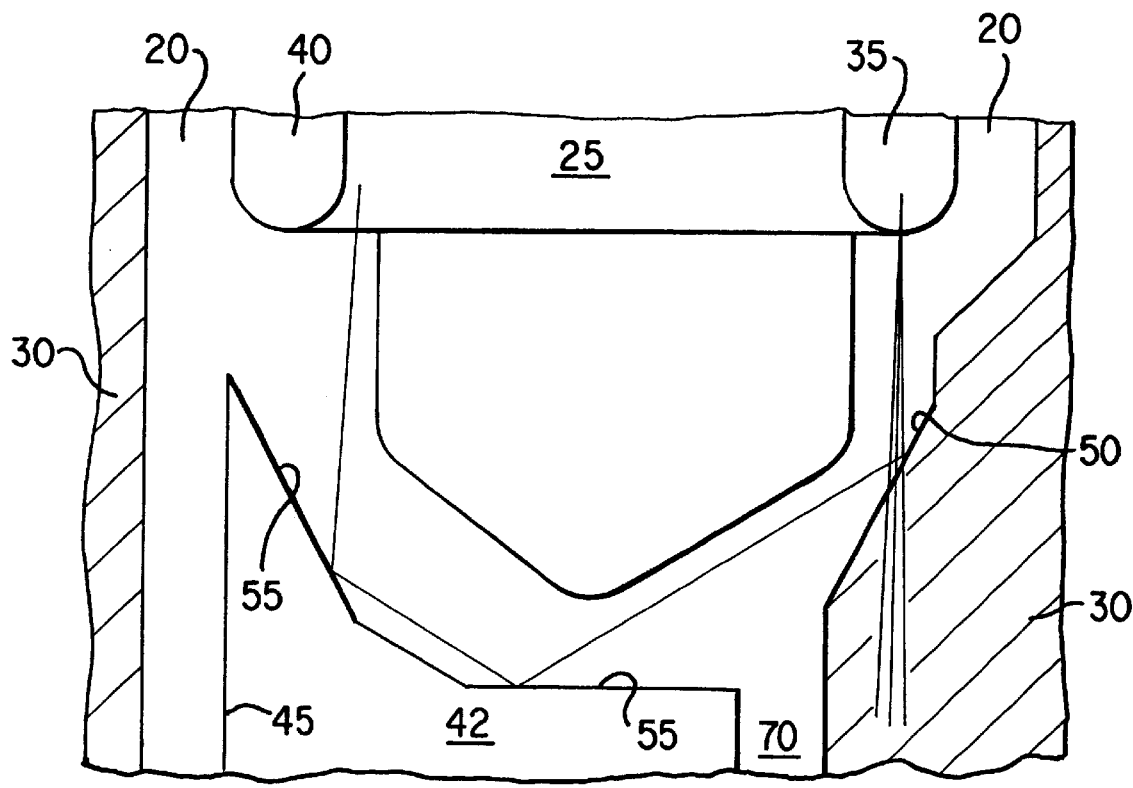
FIG. 5 is a schematic representation of light transmission patterns within a housing when a battery is in a charged state according to one preferred embodiment of the invention.

As shown in FIGS. 3–5, light source 35 is preferably positioned within cavity 25. Light source 35 preferably comprises a light emitting diode (LED) or other similar light source capable of generating a constant low- to medium-intensity light beam requiring low input current.

According to one preferred embodiment of this invention, sensing surface 50 is positioned within cavity 25. As shown in FIGS. 3–5, sensing surface 50 divides cavity 25 from interior 30 of the battery. Additionally, sensing surface 50 is preferably positioned between light source 35 and interior 30 of the battery. Sensing surface 50 is preferably generally translucent, or of a predetermined translucence. Therefore, interior 30 of the battery is optically visible from cavity 25 of device through sensing surface 50.

Sensing surface 50 is preferably positioned at an angle between approximately 59° and 63° from a normal of incoming light. Such an angle optimizes light refraction from housing material, such as SAN, to the electrolyte such as sulfuric acid.

As shown in FIGS. 3–5, at least one reflecting surface 55 is preferably positioned adjacent to sensing surface 50. reflecting surface 55 is preferably positioned and configured to reflect a maximum amount of light from light source 35 and/or sensing surface 50. An optimal mirror for light reflection is created when reflecting surface 55 is adjacent an air gap. Light is lost during transmission when reflecting surface 55 is contiguous with interior 30 of the battery or when reflecting surface is adjacent solid material of housing 20. According to another preferred embodiment of this invention, no reflecting surfaces are positioned adjacent sensing surface 50.

Therefore, as shown in FIGS. 1–5, box 45 is preferably formed with respect to housing 20. Box 45 is preferably positioned so that at least one reflecting surface 55 divides box 45 from cavity and so that reflecting surface 55 is positioned between box 45 and light source 35. According to one preferred embodiment of this invention, box 45 is filled with gas 42, such as air, and then sealed using plug 47 or similar seal known to those having ordinary skill in the art. Plug 47 or other similar seal prevents contamination in box 45 from interior 30 of the battery.

Light receiving device 40 is preferably positioned within cavity 25 of housing 20. Light receiving device 40 is positioned so that light projected from light source 35 is transmitted from sensing surface 50 to at least one reflecting surface 55 and finally to light receiving device 40. Light source 35 is preferably not directly exposed to light receiving device 40 but instead separated from light receiving device within cavity 25 of housing 20.

According to one preferred embodiment of this invention, light receiving device 40 comprises a photodiode. Light receiving device 40 may comprise a photocell or any other device that provides a signal in response to light and is of sufficient size for placement within housing 20. Alternatively, light receiving device 40 may comprise a fiber optic cable or other means for transmitting light to another location.

By containing all necessary electronics and optics within housing 20, light loss from sources other than refraction is avoided. Therefore, a more accurate and predictable reading is obtainable. In one preferred embodiment of this invention shown schematically in FIGS. 4 and 5, reflecting surface 55 comprises three separate surfaces which would otherwise result in cubed light losses if all necessary reflecting surfaces were not contained within box 45.

As shown in FIGS. 4 and 5 according to one preferred embodiment of this invention, sensing surface 50 is spaced apart from reflecting surface 55 to form optical void 70 within housing 20. Optical void 70 directs unwanted light within a predetermined range of angles out of housing 20 and away from reflecting surface 55.

FIGS. 4 and 5 show schematically the transmission of light according to two different battery charge states. Light is indicated by the lines emitting from light source 35. FIG. 4 shows a battery in a depleted charge state. Light projected from light source 35 is transmitted to sensing surface 50, where very little, if any, of the light is refracted out of housing 20. As shown, most of the light is reflected to the reflecting surfaces 55 because of the low index of refraction present in the electrolyte in interior 30 of the discharged battery. Much of the remaining light is reflected to light receiving device 40. A level of charge is thereby determined based upon the large amount of light sensed by light receiving device 40.

FIG. 5 shows a battery in a fully charged state. Light projected from light source 35 is transmitted to sensing surface 50, where most of the light is refracted. As shown, very little of the light is reflected to the reflecting surfaces 55 because of the high index of refraction present in the electrolyte in interior 30 of the fully charged battery. The remaining light is reflected to light receiving device 40. A level of charge is thereby determined based upon the small amount of light sensed by light receiving device 40.

According to one preferred embodiment of this invention, light receiving device 40 is in communication with a computer (not shown), such as an automobile's on-board computer. As shown schematically in FIG. 3 light receiving device 40 is connected with respect to controller 65 positioned within housing 20. In one preferred embodiment of this invention, controller 65 accepts a signal from light receiving device 40 and transmits appropriate information via output 75 to the computer for processing and possible feedback.

As shown in FIG. 3, according to another preferred embodiment of this invention, temperature sensor 60 is positioned within cavity 25. In addition to light receiving device 40, temperature sensor 60 is preferably also in communication with the computer. A typical voltage regulator in an automobile flat lines at approximately 13.5 volts when a normal operating temperature is reached. A fully charged battery generally requires only about 12.7 volts to maintain a steady state of charge. Any excess voltage applied to the battery will cause current to flow. Such current results in a high gassing rate and a resulting generation of internal heat in the battery.

Battery life may be reduced when the battery charges at high temperatures. Optimally, the battery does not charge while exposed to such high temperatures. Temperature sensor 60 and light receiving device 40 therefore preferably communicate with controller 65 to read an internal temperature of the battery together with a level of charge of the battery. The controller 65 preferably generates a signal based upon the internal temperature and the level of charge and if necessary generates a signal to the computer via output 75 that turns the battery off at a specified state of charge. This system would therefore result in optimum battery life and optimum battery operating conditions.

According to one preferred embodiment of this invention, output 75 comprises a 5 volt wire, a ground wire, a state of charge signal wire and a temperature signal wire. Accordingly, output 75 is preferably the only component of device 10 that is external to housing 20. An interface between output 75 and housing 20 is preferably sealed to maintain the integrity of the internal components within cavity 25 of housing 20.

While in the foregoing specification this invention has been described in relation to certain preferred embodiments thereof, and many details have been set forth for purpose of illustration, it will be apparent to those skilled in the art that the device according to this invention are susceptible to additional embodiments and that certain of the details described herein can be varied considerably without departing from the basic principles of the invention.

We claim:

1. An optical-electronic device measuring a charge level in a battery, the device comprising:
   a housing positioned within an interior of the battery, the housing having a cavity;
   a light source positioned within the cavity;
   a sensing surface positioned within the cavity, the sensing surface dividing the cavity from the interior of the battery;
   at least one reflecting surface positioned adjacent to the sensing surface;
   a box projecting outwardly from the housing and into the interior of the battery, the at least one reflecting surface directly adjacent an interior of the box and dividing the interior of the box from the cavity; and
   a light receiving device positioned within the cavity so that light projected from the light source is transmitted from the sensing surface to the at least one reflecting surface and the light receiving device.

2. The device of claim 1 wherein the sensing surface is positioned at an angle between approximately 59° and 63° from a normal of incoming light.

3. The device of claim 1 wherein the box is sealed to form an air gap and prevent contamination from the interior of the battery.

4. The device of claim 1 further comprising a computer in communication with the light receiving device.

5. The device of claim 1 further comprising a temperature sensor positioned within the cavity.

6. The device of claim 5 further comprising a computer in communication with the temperature sensor and the light receiving device.

7. The device of claim 1 wherein the light source comprises an LED.

8. The device of claim 1 wherein the light receiving device comprises a photodiode.

9. The device of claim 1 further comprising a controller positioned within the housing, the controller in communication with the light receiving device.

10. The device of claim 1 wherein the sensing surface and the reflecting surface are spaced apart to form an optical void within the housing.

11. A device for measuring a charge level in a battery, the device comprising:
    a housing positioned within an interior of the battery;
    a box extending outwardly from a lower surface of the housing;
    a light source positioned within the housing; and
    a light receiving device positioned within the housing, the light receiving device sensing light reflected through the housing directly adjacent the box and not light refracted into the interior of the battery.

12. The device of claim 11 further comprising a sensing surface positioned between the light source and the interior of the battery.

13. The device of claim 1 further comprising at least one reflecting surface positioned between the box and the light source.

14. The device of claim 12 further comprising at least one reflecting surface positioned adjacent the sensing surface.

15. The device of claim 14 wherein the at least one reflecting surface and the sensing surface are spaced apart to form an optical void within the housing.

16. A method for measuring a charge of a battery comprising:
    positioning a housing within an interior of the battery;
    transmitting light from a light source through the housing;
    refracting a portion of the light from the housing into the interior of the battery;
    reflecting a remaining portion of the light across a light reflecting surface adjacent an air gap in the interior of the battery and into a light receiving device within the housing;
    measuring the charge of the battery based upon the amount of light measured by the light receiving device.

17. The method of claim 16 further comprising controlling a voltage regulator to the battery based upon the charge of the battery.

18. The method of claim 16 further comprising measuring a temperature of the interior of the battery.

19. The method of claim 18 further comprising controlling an output of the battery based upon the temperature of the interior of the battery and the charge of the battery.

20. An optical-electronic device measuring a charge level in a battery, the device comprising:
    a housing positioned within an interior of the battery, the housing having a cavity;
    a light source positioned within the cavity;
    a sensing surface positioned within the cavity, the sensing surface dividing the cavity from the interior of the battery;
    a box extending from outside of the housing and into the interior of the battery;
    a reflecting surface positioned within the cavity and directly adjacent the box; and
    a light receiving device positioned within the cavity so that light projected from the light source is transmitted from the sensing surface to the reflecting surface and then to the light receiving device.

21. The optical-electronic device of claim 20 further comprising at least one additional reflecting surface positioned between the sensing surface and the light receiving device.

22. An optical-electronic device measuring a charge level in a battery, the device comprising:
    a housing positioned within an interior of the battery, the housing having a cavity;

a light source positioned within the cavity;

a sensing surface positioned within the cavity, the sensing surface dividing the cavity from the interior of the battery;

at least one reflecting surface positioned adjacent to the sensing surface;

a light receiving device positioned within the cavity so that light projected from the light source is transmitted from the sensing surface to the at least one reflecting surface and the light receiving device; and a temperature sensor positioned within the cavity.

23. An optical-electronic device measuring a charge level in a battery, the device comprising:

a housing positioned within an interior of the battery, the housing having a cavity;

a light source positioned within the cavity;

a sensing surface positioned within the cavity, the sensing surface dividing the cavity from the interior of the battery;

at least one reflecting surface positioned adjacent to the sensing surface;

a light receiving device positioned within the cavity so that light projected from the light source is transmitted from the sensing surface to the at least one reflecting surface and the light receiving device; and a controller positioned within the housing, the controller in communication with the light receiving device.

24. A method for measuring a charge of a battery comprising:

positioning a housing within an interior of the battery;

transmitting light from a light source through the housing;

refracting a portion of the light from the housing into the interior of the battery;

reflecting a remaining portion of the light into a light receiving device within the housing;

measuring the charge of the battery based upon the amount of light measured by the light receiving device; and controlling a voltage regulator to the battery based upon the charge of the battery.

* * * * *